(12) United States Patent
Shalon et al.

(10) Patent No.: US 7,008,532 B2
(45) Date of Patent: Mar. 7, 2006

(54) CHROMATOGRAPHIC DEVICE HAVING AN ELONGATE ROD AND METHOD OF FORMING AND CHROMATOGRAPHIC DEVICE

(75) Inventors: Yehuda Shalon, Palo Alto, CA (US); Charles F. Laub, San Jose, CA (US)

(73) Assignee: Alltech Associates Inc., Columbia, MD (US)

( * ) Notice: Subject to any disclaimer, the term of this patent is extended or adjusted under 35 U.S.C. 154(b) by 227 days.

(21) Appl. No.: 10/122,275

(22) Filed: Apr. 12, 2002

(65) Prior Publication Data

US 2003/0194814 A1    Oct. 16, 2003

(51) Int. Cl.
B01D 15/08    (2006.01)
(52) U.S. Cl. .................... 210/198.2; 210/656
(58) Field of Classification Search ............... 210/635, 210/656, 657, 659, 198.2, 232, 238; 141/12, 141/73, 80; 95/82; 96/101
See application file for complete search history.

(56) References Cited

U.S. PATENT DOCUMENTS

| | | | |
|---|---|---|---|
| 3,684,010 A * | 8/1972 | Young .................... 166/129 |
| 4,350,595 A | 9/1982 | Gunkel ..................... 210/656 |
| 4,361,482 A | 11/1982 | Teetz et al. ............... 210/198.2 |
| 4,451,365 A | 5/1984 | Sattler et al. ............. 210/198.2 |
| 4,597,866 A | 7/1986 | Couillard ................ 210/198.2 |
| D285,290 S | 8/1986 | Shalon et al. .............. D10/81 |
| 4,671,312 A * | 6/1987 | Bruton .................. 137/315.29 |
| 4,675,105 A | 6/1987 | Martin et al. ............. 210/198.2 |
| 4,710,289 A | 12/1987 | Wermuth et al. ........ 210/198.2 |
| 4,719,011 A | 1/1988 | Shalon et al. ............. 210/198.2 |
| 4,737,292 A | 4/1988 | Ritacco et al. ............. 210/656 |
| 4,769,141 A | 9/1988 | Couillard ................ 210/198.2 |
| 4,865,728 A | 9/1989 | Larsson .................... 210/198.2 |
| 4,882,047 A | 11/1989 | Shalon .................... 210/198.2 |
| 4,891,133 A | 1/1990 | Colvin, Jr. ................ 210/198.2 |
| 5,137,628 A | 8/1992 | Hart et al. ................ 210/198.2 |
| 5,169,522 A | 12/1992 | Shalon et al. ............. 210/198.2 |
| 5,192,433 A | 3/1993 | Shalon .................... 210/198.2 |
| 5,213,683 A | 5/1993 | Mann ....................... 210/198.2 |
| 5,366,621 A | 11/1994 | Bidell et al. .............. 210/198.2 |
| 5,378,361 A | 1/1995 | Baeckstrum ............. 210/198.2 |
| 5,423,982 A | 6/1995 | Jungbauer et al. ........ 210/198.2 |
| 5,462,659 A | 10/1995 | Saxena et al. ............ 210/198.2 |
| 5,531,810 A | 7/1996 | Fullemann .................... 96/105 |
| 5,866,008 A | 2/1999 | Shalon et al. ................ 210/656 |
| 5,893,971 A | 4/1999 | Shalon et al. ............. 210/198.2 |
| 5,951,873 A | 9/1999 | Shalon et al. ................ 210/656 |

(Continued)

FOREIGN PATENT DOCUMENTS

EP    0040663 A1    2/1981    ............. 210/198.2

(Continued)

Primary Examiner—Ernest G. Therkorn
(74) Attorney, Agent, or Firm—William D. Bunch

(57) ABSTRACT

A chromatographic device comprises a chromatographic tube, a chromatographic medium, a piston assembly, an elongate rod, and a threaded member. The piston assembly is within the tube and is positioned generally between a first end of the tube and the chromatographic medium. The chromatographic medium is generally between the piston assembly and a second end of the tube. The elongate rod extends partially into the chromatographic tube such that the piston assembly is between the elongate rod and the second end of the chromatographic tube. The elongate rod has a threaded outer surface. The threaded member is threaded to the threaded outer surface of the elongate rod. The treaded member is operatively secured to the chromatographic tube.

10 Claims, 1 Drawing Sheet

U.S. PATENT DOCUMENTS

| | | | |
|---|---|---|---|
| 6,036,855 A | 3/2000 | Shalon et al. | 210/198.2 |
| 6,125,541 A * | 10/2000 | Parker | 29/898.051 |
| 6,171,486 B1 | 1/2001 | Green et al. | 210/198.2 |

FOREIGN PATENT DOCUMENTS

| | | | |
|---|---|---|---|
| EP | 0040663 B1 | 9/1986 | 210/198.2 |

* cited by examiner

CHROMATOGRAPHIC DEVICE HAVING AN ELONGATE ROD AND METHOD OF FORMING AND CHROMATOGRAPHIC DEVICE

BACKGROUND OF THE INVENTION

This invention relates to the field of liquid chromatography, and more particularly to chromatographic devices having pistons for compressing a chromatographic medium.

Chromatography is a method of separating individual compounds in a mixture by distributing the compounds between heterogenous phases. A column packing material (or media), forming a stationary phase, generally has a large surface area through which a liquid mobile phase is allowed to flow. Chemical compounds in the mobile phase are maintained in the system for a time that is dependent upon the affinity of the particular compounds for the stationary phase. Multiple component mixtures can, with chromatography, be separated into single components in a single step procedure.

Chromatographic separations can be carried out efficiently in columns slurry packed with microparticulate media. The slurry is uniformly and rapidly compacted into a column under pressure. The slurry is maintained at high pressure and density to achieve efficient end results.

A chromatographic device generally includes a chromatographic column (having a cylindric column body and a fixed end plate covering one end of the column body), a piston slidable within the column body, an intake opening through the piston, a discharge opening through the end plate, a first porous frit seated within a frit-receiving socket of the piston and covering the intake opening, and a second porous frit secured to the end plate and covering the discharge opening. A slurry containing the packing material, such as a granular silica or polymeric media, is placed within the column body and the piston is moved toward the fixed end plate to compress the slurry. The pores of the frits are sized to permit the liquid of the slurry to flow out the discharge opening while preventing discharge of the packing material. Conventionally, when the chromatographic media within a chromatographic column is packed, a telescoping rod of a hydraulic pushing device pushes the piston into the column. This compression packs the packing material to a predetermined pressure (which may typically be around 1,000 to 5,000 p.s.i., but these values are merely exemplary rather than limiting).

With such conventional method of packing chromatographic columns, the column remains attached to the pushing device so that the rod of the hydraulic pushing device maintains the pushing force on the piston. In other words, the column must remain attached to the pushing device during operation of the chromatographic column, i.e., during chromatographic separations.

SUMMARY OF THE INVENTION

Among the several objects of the present invention may be noted the provision of an improved chromatographic device and method for forming a chromatographic device; the provision of such a device and method for forming a chromatographic device in which compression is maintained on a column piston even after removal of the column from a pushing device; and the provision of such a device and method for forming a chromatographic device which is reliable and yet relatively inexpensive.

Generally, a chromatographic device of the present invention comprises a chromatographic tube, a chromatographic medium, a piston assembly, an elongate rod, and a threaded member. The chromatographic tube comprises first and second opposite ends and an inner surface. The inner surface of the tube at least in part defines an intermediate region. The intermediate region is generally between the first and second ends. The chromatographic medium is within the intermediate region. The piston assembly is within the tube and is positioned generally between the first end of the tube and the chromatographic medium. The piston assembly defines a passage for flow of process fluid. The chromatographic medium is generally between the piston assembly and the second end of the tube. The elongate rod extends partially into the chromatographic tube such that the piston assembly is between the elongate rod and the second end of the chromatographic tube. The elongate rod has a threaded outer surface. The threaded member is threaded to the threaded outer surface of the elongate rod. The treaded member is operatively secured to the chromatographic tube.

A chromatographic device of another aspect of the present invention comprises a chromatographic tube, a chromatographic medium, a piston assembly, an elongate rod, and a rod flange. The chromatographic tube comprises first and second opposite ends and an inner surface. The inner surface of the tube at least in part defines an intermediate region. The intermediate region is generally between the first and second ends. The chromatographic medium is within the intermediate region. The piston assembly is within the tube and positioned generally between the first end of the tube and the chromatographic medium. The piston assembly defines a passage for flow of process fluid. The chromatographic medium is generally between the piston assembly and the second end of the tube. The elongate rod extends partially into the chromatographic tube such that the piston assembly is between the elongate rod and the second end of the chromatographic tube. The rod flange is attached to the elongate rod. The rod flange is operatively secured to the chromatographic tube.

A method of the present invention for forming a chromatographic device comprises providing a chromatographic tube having a first end and a second end opposite the first end. The chromatographic tube extends longitudinally along a tube axis. The method further comprises: placing a chromatographic medium in the chromatographic tube, inserting a piston assembly into the chromatographic tube such that the chromatographic medium is between the piston assembly and the second end of the tube, and partially inserting an elongate rod into the chromatographic tube such that the piston assembly is between the elongate rod and the second end of the chromatographic tube. The elongate rod has a threaded outer surface. The elongate rod is moved generally along the tube axis and toward the second end of the chromatographic tube in a manner to move the piston assembly relative to the chromatographic tube toward the second end of the chromatographic tube to thereby compress the chromatographic medium. The threaded member is threaded onto the threaded outer surface of the elongate rod and operatively locked to the chromatographic tube.

Another method of the present invention for forming a chromatographic device comprises providing a chromatographic tube having a first end and a second end opposite the first end. The chromatographic tube extends longitudinally along a tube axis. The method further comprises: placing a chromatographic medium in the chromatographic tube, inserting a piston assembly into the chromatographic tube such that the chromatographic medium is between the piston assembly and the second end of the tube, and partially inserting an elongate rod into the chromatographic tube such that the piston assembly is between the elongate rod and the second end of the chromatographic tube. The elongate rod is moved generally along the tube axis and toward the second end of the chromatographic tube in a manner to move the piston assembly relative to the chromatographic tube toward the second end of the chromatographic tube to thereby compress the chromatographic medium. The rod flange is attached to the elongate rod such that the rod flange extends radially outwardly from the elongate rod. The rod flange is also operatively locked to the chromatographic tube.

Other objects and features will be in part apparent and in part pointed out hereinafter.

BRIEF DESCRIPTION OF THE DRAWING

Corresponding reference characters indicate corresponding parts throughout the drawing.

DESCRIPTION OF THE PREFERRED EMBODIMENTS

Figure 1:
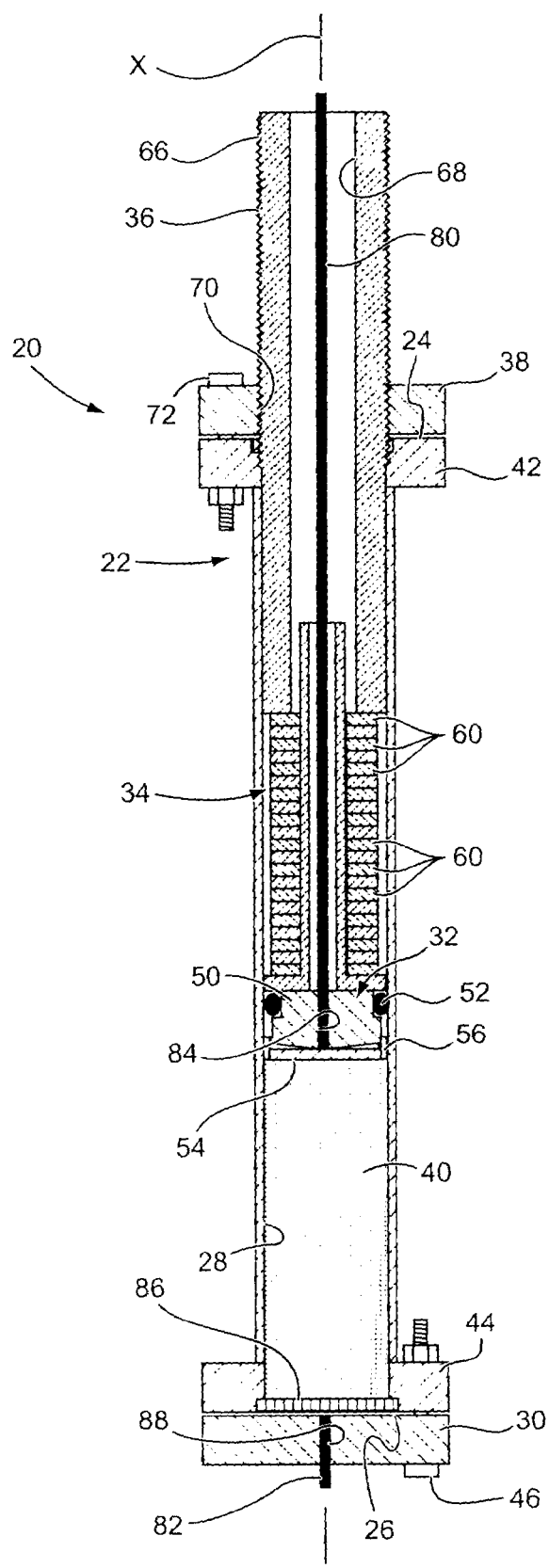
FIG. 1 is a longitudinal section view of a chromatographic column of the present invention.

Referring now to FIG. 1, a chromatographic device of the present invention is indicated in its entirety by the reference numeral 20. The chromatographic device (or column) 20 comprises a chromatographic tube 22 extending longitudinally along a tube axis X. The tube 22 comprises first and second opposite ends 24, 26, and an inner surface 28. Preferably, the first end 24 of the tube 22 is open and the second end 26 is closed. The inner surface 28 of the tube 24 at least in part defines an intermediate region of the tube. The intermediate region is generally between the first and second ends 24, 26. The chromatographic column 20 preferably further comprises an end plate 30, a piston assembly, generally indicated at 32, a spring mechanism, generally indicated at 34, an elongate rod 36, a rod flange 38, and a chromatographic medium 40.

Preferably, the chromatographic tube 22 further comprises a first tube flange 42 adjacent the first end 24 of the tube and a second tube flange 44 adjacent the second end 26 of the tube. Preferably, each of the tube flanges 42, 44 extends generally radially outwardly relative to the tube axis X. The end plate 30 is preferably secured to the second tube flange 44 via a plurality of bolts 46 (only one of which is shown in FIG. 1) to close the second end 26 of the tube 22.

The piston assembly 32 comprises a piston body portion 50, an o-ring seal 52, a frit 54, and a flexible sleeve 56 securing the frit to the piston body portion. Preferably the o-ring seal 52 is of Viton® encapsulated in a polytetrafluoroethylene (PTFE or Teflon®) coating. The o-ring seal 52 circumscribes the piston body portion 50 and rests in a circumferential groove in the piston body portion. In operation, the frit 54 is generally between the end of the piston body portion 50 and the chromatographic medium 40. The flexible sleeve 56 preferably comprises a polymeric material (e.g., PTFE), and more preferably comprises a heat-shrinkable material (e.g., a heat-shrinkable PTFE). The flexible sleeve 56 circumscribes the periphery of the frit 54 and the end margin of the piston body portion 50 to secure the frit to the piston body portion and to seal against fluid leakage between the frit and the piston body portion. Preferably, the flexible sleeve 56 is heat shrunk on the frit 54 and end margin of the piston body portion 50 to form a snug fit of the sleeve around the frit and end margin of the piston body portion. Preferably, the end margin of the piston body portion 50 includes a plurality of relatively sharp circumferential ridges (not shown) shaped and adapted to grip the flexible sleeve 56 to prevent movement of the sleeve and frit 54 relative to the piston body portion. Preferably, the frit 54 is attached to the piston body portion 50 in the manner described in co-pending and commonly assigned U.S. patent application Ser. No. 10/114,528, filed Apr. 2, 2002, and entitled Chromatographic Device and Method of Forming a Chromatographic Device (incorporated herein by reference).

The spring mechanism 34 is positioned between the elongate rod 36 and the piston assembly 32. Preferably, the spring mechanism 34 comprises a plurality of stacked bellville washers 60. Alternatively, the spring mechanism 34 may comprise one or more helical springs or any other suitable type of compression spring mechanism.

The elongate rod 36 extends partially into the chromatographic tube 22 such that the piston assembly 32 and the spring mechanism 34 are axially between the elongate rod and the second end 26 of the tube. Preferably, the elongate rod 36 includes a threaded outer surface 66. Also preferably, the elongate rod 36 comprises a pipe having an elongate bore 68 extending along the entire length of the rod. As discussed in greater detail below, the elongate rod 36 presses against the spring mechanism 34 which presses against the chromatographic medium 40 to compact the chromatographic medium.

The elongate rod 36 is secured to the chromatographic tube 22 via the rod flange 38. The rod flange 38 preferably has a threaded bore 70 sized and adapted to threadably mate with the threaded outer surface 66 of the elongate rod 36. Thus, the rod flange 38 with its threaded bore 70 constitutes a threaded member. The rod flange 38 is sized and adapted to abut the first tube flange 42 of the chromatographic tube 22 and is preferably secured thereto with three bolts 72 (only one of which is shown in FIG. 1). Each bolt 72 extends through aligned bores in the first tube flange 42 and the rod flange 38 to lock the rod flange against the first tube flange. With the threaded outer surface 66 of the elongate rod 36 threaded into the threaded bore 70 of the rod flange 38, and with the rod flange secured to the first tube flange 42, the elongate rod 36 prevents the piston assembly 32 from moving longitudinally toward the first end of the chromatographic tube 22.

The chromatographic column 20 further comprises first and second process fluid lines 80, 82. The first process fluid line 80 has first and second opposite ends and an intermediate region. The first end of the first process fluid line 80 is preferably attached to the piston assembly 32 via a suitable connector, such as a compression fitting (not shown), so that the first process fluid line is in fluid communication with a flow passage 84 of the piston assembly. The first fluid line 80 extends through the elongate bore 68 of the elongate rod 36 and through each of the beliville washers 60 of the spring mechanism 34. Thus, the intermediate region of the process fluid line is within the elongate bore 68 and the second end of the process fluid line is outside of the chromatographic column 20. An end frit 86 is secured between the end plate 30 and the second tube flange 44. The second process fluid line 82 is preferably attached to the end plate 30 via a suitable compression fitting (not shown) so that the second process fluid line is in fluid communication with a flow passage 88 extending through the end plate.

To form the chromatographic column 20, the chromatographic medium 40, preferably in the form of a slurry, is poured through the open first end 24 of the chromatographic tube 22 or otherwise placed into the tube. The piston assembly 32 is inserted into the chromatographic tube 22 such that the chromatographic medium 40 is axially between the piston assembly and the second end 26 of the tube. The spring mechanism 34 is inserted into the chromatographic tube 22 such that the piston assembly is axially positioned between the spring mechanism and the chromatographic medium 40. The elongate rod 36 is partially inserted into the chromatographic tube 22 such that the piston assembly 32 is between the elongate rod and the second end 26 of the tube. Preferably, the first process fluid line 80 is fed through both the bore of the elongate rod 36 and the spring mechanism 34 and attached to the piston assembly 32 before the spring mechanism and elongate rod are inserted into the chromatographic tube 22. Force is applied to the elongate rod 36 via a suitable pusher mechanism (not shown) to move the elongate rod generally along the tube axis X and toward the second end 26 of the tube to thereby compress the chromatographic medium 40. The rod flange 38 is threaded onto the threaded outer surface 66 of the elongate rod 36. The rod flange 38 is then turned (rotated) relative to the elongate rod 36 to a point where the rod flange 38 abuts the first tube flange 42. The rod flange 38 is then locked to the tube flange 42 via the bolts 72. Preferably, the rod flange 38 is locked to the tube flange after the elongate rod 36 is moved axially to compress the chromatographic medium. After the rod flange 38 is locked to the tube flange 42, the chromatographic column 20 is removed from the pusher mechanism. Thus, the locked elongate rod 36 in conjunction with the spring mechanism 34 maintains compression on the chromatographic medium 40.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A chromatographic device comprising:
    a chromatographic tube comprising first and second opposite ends, and an inner surface, the inner surface of the tube at least in part defining an intermediate region, the intermediate region being generally between the first and second ends;
    a chromatographic medium within the intermediate region;
    a piston assembly within the tube and positioned generally between the first end of the tube and the chromatographic medium, the piston assembly defining a passage for flow of process fluid, the chromatographic medium being generally between the piston assembly and the second end of the tube;
    an elongate rod comprising an elongate bore, the rod extending partially into the chromatographic tube such that the piston assembly is between the elongate rod and the second end of the chromatographic tube, the elongate rod having a threaded outer surface;
    a threaded member threaded to the threaded outer surface of the elongate rod, the threaded member being operatively secured to the chromatographic tube.

2. A chromatographic device as set forth in claim 1 wherein the chromatographic tube further comprises a flange adjacent the first end of the tube, the flange extending generally radially outwardly relative to the tube axis, and the threaded member being operatively secured to the flange.

3. A chromatographic device as set forth in claim 1 wherein the elongate rod comprises a pipe having an elongate bore, the outside diameter of the pipe being contiguous with the tube.

4. A chromatographic device as set forth in claim 3 further comprising a process fluid line, the process fluid line having first and second opposite ends and an intermediate region between the first and second ends, the first end of the process fluid line being operatively attached to the piston assembly such that the process fluid line is in fluid communication with the flow passage of the piston assembly, the intermediate region of the process fluid line being within the elongate bore of the pipe and the second end of the process fluid line being outside of the pipe.

5. A chromatographic device comprising:
    a chromatographic tube comprising first and second opposite ends, and an inner surface, the inner surface of the tube at least in part defining an intermediate region, the intermediate region being generally between the first and second ends;
    a chromatographic medium within the intermediate region;
    a piston assembly within the tube and positioned generally between the first end of the tube and the chromatographic medium, the piston assembly defining a passage for flow of process fluid, the chromatographic medium being generally between the piston assembly and the second end of the tube;
    an elongate rod comprising an elongate bore, the rod extending partially into the chromatographic tube such that the piston assembly is between the elongate rod and the second end of the chromatographic tube;
    a rod flange attached to the elongate rod, the rod flange being operatively secured to the chromatographic tube.

6. A chromatographic device as set forth in claim 5 wherein the chromatographic tube further comprises a tube flange adjacent the first end of the tube, the tube flange extending generally radially outwardly relative to the tube axis, and the rod flange being operatively secured to the tube flange.

7. A chromatographic device as set forth in claim 5 wherein the elongate rod comprises a pipe having an elongate bore, the outside diameter of the pipe being contiguous with the tube.

8. A chromatographic device as set forth in claim 7 further comprising a process fluid line, the process fluid line having first and second opposite ends and an intermediate region between the first and second ends, the first end of the process fluid line being operatively attached to the piston assembly such that the process fluid line is in fluid communication with the flow passage of the piston assembly, the intermediate region of the process fluid line being within the elongate bore of the pipe and the second end of the process fluid line being outside of the pipe.

9. A chromatographic device as set forth in claim 5 further comprising a spring mechanism positioned axially between the piston assembly and the elongate rod.

10. A chromatographic device as set forth in claim 9 wherein the spring mechanism comprises a plurality of bellville washers.

* * * * *